United States Patent
Lissek et al.

(10) Patent No.: US 7,837,635 B2
(45) Date of Patent: Nov. 23, 2010

(54) DEVICE AND METHOD FOR DETERMINING AT LEAST ONE CHARACTERISTIC POINT OF JOINT TO BE ORTHOPEDICALLY MEASURED

(75) Inventors: Karsten Lissek, Munich (DE); Urs Schneider, Stuttgart (DE); Kai Von Lübtow, Stuttgart (DE); Markus Haid, Stuttgart (DE); Alfons Fuchs, Dossenheim (DE); Roland Bauernfeind, München (DE)

(73) Assignee: Fraunhofer-Gesellschaft zur Förderung der Angewandten Forschung E.V., München (DE)

( * ) Notice: Subject to any disclaimer, the term of this patent is extended or adjusted under 35 U.S.C. 154(b) by 0 days.

(21) Appl. No.: 11/667,891

(22) PCT Filed: Nov. 7, 2005

(86) PCT No.: PCT/EP2005/011917

§ 371 (c)(1),
(2), (4) Date: Jan. 4, 2008

(87) PCT Pub. No.: WO2006/053650

PCT Pub. Date: May 26, 2006

(65) Prior Publication Data

US 2008/0221485 A1 Sep. 11, 2008

(30) Foreign Application Priority Data

Nov. 16, 2004 (DE) .................. 10 2004 055 234

(51) Int. Cl.
*A61B 5/103* (2006.01)
(52) U.S. Cl. ........................ 600/595; 600/587
(58) Field of Classification Search ............... 600/587, 600/595
See application file for complete search history.

(56) References Cited

U.S. PATENT DOCUMENTS 4,306,571 A 12/1981 McLeod, Jr.

(Continued)

FOREIGN PATENT DOCUMENTS

DE 100 14 397 10/2001

(Continued)

OTHER PUBLICATIONS

"Polyzentrische Gelenke in der Prothetik—Eigenschaften und Einsatzbereiche", Kaphingst et al., Orthopadie-Technik 7/01, pp. 484-490 (English language abstract on p. 1).

(Continued)

*Primary Examiner*—Max Hindenburg
*Assistant Examiner*—Michael C Stout
(74) *Attorney, Agent, or Firm*—McCracken & Frank LLP (57) ABSTRACT

A device determines at least one characteristic point of a joint which joins together two limbs and is to be measured orthopedically comprising a first coupling element which may be positioned on a first limb adjoining the joint, a second coupling element which may be moved relative to the first coupling element and may be positioned on a second limb adjoining the joint, and a measuring device for determining the position of the first coupling element relative to the second coupling element. The measuring device has at least one reference point rigidly connected to one of the first and second coupling elements, and a reference point detection device rigidly connected to the respective other of the first and second coupling elements. During a movement of the first and second limbs with respect to one another the reference point detection device determines the at least one characteristic point.

12 Claims, 5 Drawing Sheets

U.S. PATENT DOCUMENTS

| | | | |
|---|---|---|---|
| 4,436,099 A | | 3/1984 | Raftopoulos |
| 5,496,304 A | * | 3/1996 | Chasan .......................... 606/1 |
| 6,264,665 B1 | * | 7/2001 | Yu et al. ..................... 606/130 |
| 6,692,447 B1 | * | 2/2004 | Picard ........................ 600/587 |
| 7,107,832 B2 | | 9/2006 | Blumentritt et al. |
| 2003/0083596 A1 | * | 5/2003 | Kramer et al. ............. 600/595 |
| 2004/0106861 A1 | * | 6/2004 | Leitner ....................... 600/407 |

FOREIGN PATENT DOCUMENTS

| | | |
|---|---|---|
| EP | 1 454 584 | 9/2004 |
| WO | WO 94/07108 | 3/1994 |
| WO | WO 03/047430 | 6/2003 |

OTHER PUBLICATIONS

"Systematik der Kniegelenkorthetik", Grifka, Orthopadie-Technik 5/95, pp. 389-397 (English language abstract on p. 1).

"Anwendung des L.A.S.A.R. Posture in der Beinorthetik", Drewitz et al., Orthopadie-Technik 2/00, pp. 92-101 (English language abstract on p. 1).

International Search Report and Written Opinion in PCT/EP2005/011917 dated Feb. 27, 2006.

International Preliminary Examination Report in PCT/EP2005/011917 dated Jan. 30, 2007.

* cited by examiner

DEVICE AND METHOD FOR DETERMINING AT LEAST ONE CHARACTERISTIC POINT OF JOINT TO BE ORTHOPEDICALLY MEASURED

TITLE OF THE INVENTION

CROSS REFERENCE TO RELATED APPLICATIONS

Not applicable.

REFERENCE REGARDING FEDERALLY SPONSORED RESEARCH OR DEVELOPMENT

Not applicable.

SEQUENTIAL LISTING

Not applicable.

BACKGROUND OF THE INVENTION

1. Field of the Invention

The present invention relates to a device for determining at least one characteristic point of a joint which joins together two limbs and is to be measured orthopedically, the device comprising a first coupling element which may be attached to a first limb adjoining the joint, a second coupling element which may be moved relative to the first coupling element and may be attached to a second limb adjoining the joint, and a measuring device for determining the position of the first coupling element relative to the second coupling element.

2. Description of the Background of the Invention

In orthopedic technology, there are various applications in which a joint of human extremities is to be measured. It is particularly necessary in the field of joint orthotics or prosthetics to determine the dynamic behavior of joints of human extremities. Thus, for example, it is necessary to specifically adapt outhouses, which are an external stabilization aid for the mechanical and functional stabilization of joints, to the respective joint of the patient which is to be supported. A preferred application of outhouses are knee joint orthoses. These are used to stabilize the knee joint in the case of abnormal weakening or weakening as a result of an operation in the same way as they are used by competitive athletes to avoid strains. The knee joint in particular does not behave, however, like a simple hinge joint with a singular axis of rotation, but rather like a polycentric joint with a plurality of pivots, the pivot positions of which constantly change with respect to one another during a relative movement of thigh and lower leg. Although in the meantime there have been various attempts at using in orthotics and prosthetics polycentric joints which imitate more or less effectively the actual behavior of the respective human joint to be supported, monocentric joints basically continue to be used in orthoses and prostheses.

Monocentric and polycentric orthoses and prostheses have to be adapted individually to the respective patient. The result of mismatching an orthosis may be, for example, that said orthosis does not ensure the required mechanical and functional stabilization of the respective joint. Furthermore, a mismatch of an orthosis may even result in secondary damage to the joint, because this joint is additionally stressed by the resistance produced by the orthosis per se to stabilize the joint, against certain movements. To adapt the orthosis or prosthesis, therefore, a compromise pivotal point and/or a polar curve reflecting the path of instantaneous pivotal points at various bending angles of the joint have been determined hitherto. The orthosis or prosthesis is adjusted by an orthopaedic technician according to the determined compromise pivotal point or the polar curve. The Nietert method, with which a person skilled in the art is generally acquainted, is used in particular for determining the compromise pivotal point. This method produces a range within which the compromise pivotal point is to be expected. However, it has been found that a determination of this type is not sufficiently accurate, for example in reliably adapting an orthosis to every patient while avoiding mismatches.

Formerly, axes of rotation in joints were mainly measured in expensive clinical studies. In so doing, markers were preferably placed in bones of cadaver preparations and the movement thereof was traced photographically and radiologically. These measures lead to general findings in respect of the position of compromise pivotal point and polar curves on various joints, but do not assist individual adaptation of an orthosis or prosthesis to the respective patient.

Goniometers have long been used for specifically adapting orthoses to patients. A goniometer allows, for example, the extent of movement of a joint to be determined, although the use of a goniometer provides no information about the position of the axes of rotation. Reference is made to WO94/07108 concerning the construction and mode of operation of an orthopedically used goniometer. The prior art according to U.S. Pat. No. 4,306,571 also describes the possibility of using a multiple goniometer for obtaining data while stressing a knee joint.

Another approach for measuring patients is known from European patent application EP 1 454 584 A1. In this case, a patient is positioned on a support plate mounted on measuring cells and is measured by laser beams. This prior art provides in particular the production of a dynamic effect line for a patient, based on the measurement result obtained via the support plate, and a prosthesis or orthosis may be adapted using this dynamic effect line.

DE 10014397 A1 describes a device for measuring angles of joints. The device consists of two rails connected to a goniometer by a preferably fixable pivot. Positioned on these rails are contact elements, of which at least one may be moved axially to the rail. To use the device, the limbs of the body which are to be measured and are connected by a common joint are brought into the position to be measured. The contact elements are then positioned on the body limbs at defined anatomical points such that the existing angle between the rails corresponds to the angle of the joint between the body limbs. Fixing the pivot of the device facilitates the removal of the device from the body and reading off the angle of the joint, without changing the angle between the rails.

Furthermore, U.S. Pat. No. 4,436,099 describes a similar device for measuring the relative angular displacement between two body limbs connected by a common joint. In this device, two rigid rods are connected to a load cell, one of the rods being rotatable by a joint attached to the cell and the other rod being attached to the cell. The rods are each attached to one of the limbs by holding means in which the rods are able to rotate and may be moved parallel to the longitudinal axis of the relevant limb. Located in the load cell is a circuit which produces an electrical signal which is an indication of the angular displacement between the rigid rods, i.e. also of the angular displacement between the limbs. The electrical signal is further conveyed via a cable to a counter and a display. The display is appropriately installed at a distance from the body to be measured, so that it is easily possible to read the measured angular displacement between the limbs.

The document U.S. Pat. No. 6,692,447 B1 describes a system for determining pivot centers for proximal and intermediary articulations. For that purpose a signal marker is fixed to a bone, in order to determine pivot points of such proximal and intermediary articulations.

The object of the present invention is to provide a device and a method of the type mentioned at the outset, using which it is possible, with simple handling, to determine with sufficient accuracy a characteristic point of a patient's joint to be measured orthopedically.

This object is achieved by a device of the type mentioned at the outset, in which the measuring device has at least one reference point which is rigidly connected to one of the first and second coupling elements, and also has a reference point detection device which is rigidly connected to the respective other coupling element of the first and second coupling elements, the reference point detection device detecting a plurality of positions of the reference point relative to the reference point detection device where there is a movement of the first and second limbs towards one another and determining from this the at least one characteristic point.

The device according to the invention may be attached directly to the limbs joined together by the joint to be measured, i.e. it may be held thereon or secured thereto. When the coupling elements of the device according to the invention have been attached to the limbs, the limbs may be moved relative to one another while bending the joint, the joint performing its natural movements. In this manner it is possible to detect the relative movement of the two limbs with respect to one another in a substantially unstressed position of the joint as well as when the joint is fully loaded using the device according to the invention. This is carried out in that the at least one reference point rigidly connected to one of the first and second coupling elements moves with the respectively associated coupling element corresponding to the movement of the joint. This movement is detected selectively by the reference point detection device at least at a plurality of points. The characteristic point, for example a compromise centre of rotation, may then be determined from these instantaneous positions of the at least one reference point. The findings thus obtained for the position of the characteristic point, in particular the compromise centre of rotation, may then be used by an orthopaedic surgeon or an orthopaedic technician to adapt an orthosis or a prosthesis. Thus, for example, to adapt a monocentric orthosis, the pivot axis thereof may be made to correspond to the compromise axis of rotation determined by the device according to the invention in order to utilize in the best possible manner the mechanical stabilization function of the orthosis for the joint to be stabilized. Furthermore, the device according to the invention may determine a characteristic point, for example a compromise centre of rotation, for a healthy joint to be measured and a joint prosthesis may be correspondingly adapted for an extremity to be provided with a prosthesis, according to the measurement data obtained.

The invention therefore provides the possibility of measuring a joint orthopedically with sufficient accuracy and with relatively simple technical means and with a low measuring complexity, it being possible to further use the obtained measurement data for the orthotic or prosthetic care of a patient.

A development of the invention provides that the reference point detection device detects a movement path of the respective reference point from the plurality of positions of the reference point. It should be noted that with an increase in number of detected positions of the reference point, the findings obtained via the joint to be measured orthopedically become more detailed and thus a more accurate determination of the characteristic point of this joint is possible. The detected movement path may be a two-dimensional curve (projected in a plane) or a three-dimensional curve.

In a preferred embodiment of the invention, a processing system is provided which is coupled or may be coupled to the reference point detection device for transmitting data. The processing system processes in a predetermined manner the data obtained from the reference point detection device. The processing system may be configured separately from the device which may be positioned on or attached to the joint, or may also be configured integrally therewith. A development of the invention preferably provides that the processing system determines the at least one characteristic point as at least one virtual pivotal point for the joint to be measured from the data received from the reference point detection device, in particular from the movement path of the respective reference point. The determined virtual pivotal point is often also referred to by experts as a compromise pivotal point, a compromise centre of rotation or a compromise axis of rotation.

Particularly for the adjustment of polycentric joints, detailed investigations are necessary which go beyond determining a singular characteristic point, for example of the comprise centre of rotation. In this connection, a development of the invention provides that the processing system determines a plurality of characteristic points, preferably as a polar curve, for the joint to be measured from the data received from the reference point detection device, in particular from the movement path of the respective reference point. The polar curve (also called centrode) reflects the path of the instantaneous pivotal points at various bending angles of the respective joint. A polycentric orthosis or prosthesis may then be adjusted, for example, according to the determined polar curve, so that the polar curve of the orthosis corresponds substantially to the polar curve of the joint to be provided with an orthosis or that the polar curve of the polycentric prosthesis for an extremity, to be provided with a prosthesis, of a patient is adapted accordingly to the polar curve of the healthy joint of the respective other extremity of the patient to avoid asymmetric strains on the patient.

As already described above, the findings, obtained via the device according to the invention, on the characteristic point of the joint to be measured orthopedically are used in a preferred application to adjust an orthosis for the joint. This is carried out in the easiest way in that the orthosis is directly adapted in the immediate vicinity of the joint. To this end it is necessary for the determined characteristic point, for example the virtual pivotal point (compromise pivotal point) to be made visible to the joint to be measured orthopedically. For this purpose, a development of the invention provides an optical output means by which the at least one determined characteristic point of the joint may be indicated optically on the joint to be measured. This may be carried out, for example, in that the output means comprises an angled arrangement of a plurality of light sources which are able to emit preferably directed light beams, it being possible to indicate the at least one determined virtual pivotal point by a point of intersection of the two both light beams. Alternatively, the determined characteristic point of the joint may also be indicated by one or more laser beams.

As an alternative to indicating the at least one determined virtual pivotal point by light beams crossing one another in a point of intersection, it is also possible for the output means to have an arrangement of a plurality of light sources which indicate contact points in particular for positioning a gauging arrangement, in particular a ruler arrangement, it being possible to indicate the at least one determined virtual pivotal point on the joint by suitable positioning of the ruler arrangement. Individual light points are thus able to indicate coordinates for the virtual pivotal point so that it is possible to indicate and mark the determined virtual pivotal point on the joint using the rulers by the contacting of one or more rulers by an orthopaedic technician or the like using the indicated coordinates. Alternatively, the orthopaedic technician can mark out by eye the virtual pivotal point on the joint without rulers using the indication points.

As an alternative to an optical indication means using light sources, a development of the invention provides an electromechanical output means which has an electromechanically displaceable marking, it being possible to indicate the at least one determined virtual pivotal point by suitably positioning the electromechanically displaceable marking on the joint. For example, the marking may be displaced electromechanically within a specific field via one or more linear adjusting elements and the marking can then remain at the at least one determined virtual pivotal point for marking by electromechanically activating the adjusting elements according to the determined characteristic point.

An advantageous development of the invention provides a marking device, in particular a pencil, using which it is possible to make a color marking on the joint at the at least one determined virtual pivotal point after a corresponding electromechanical displacement of the marking. The device according to the invention is thus able to automatically make a marking on the patient's joint which is to be provided with an orthosis or prosthesis, which marking may then be used later on for adapting an orthosis or prosthesis.

The foregoing has generally described how it is possible to detect the actual position of the reference point using the reference point detection device. This may be carried out, for example, in that the reference point detection device optically detects the position of the at least one reference point. As an alternative or additionally to this, it may be provided that the reference point detection device electronically detects the position of the at least one reference point. For example, the position of the reference point may be determined magnetically via Hall sensors. Alternatively, it is also possible to join together the two coupling elements via a multijoint arrangement, it being possible to determine the exact relative position of the first coupling element relative to the second coupling element via rotary or linear position transmitters. Linear or rotary position transmitters of this type may be, for example, corresponding linear or rotary potentiometers. Basically, it should be noted that every technical possibility of determining the relative position of the first coupling element relative to the second coupling element, in particular of determining the relative position of at least one reference point rigidly connected to a coupling element, relative to the other coupling element, lies within the scope of the invention, provided it that it affords adequate accuracy.

The measuring accuracy of the device according to the invention may be further increased in that at least two mutually spaced apart reference points, which are rigidly connected to one of the first and second coupling elements, are monitored. In this respect, the reference point detection device detects a plurality of positions of the reference points, preferably the movement paths of the at least two reference points relative to the reference point detection device, during a movement of the first and second limb with respect to one another.

The invention also relates to a method for determining at least one characteristic point of a joint which joins together two limbs and is to be measured orthopedically, using a device, in particular of the type described above, the method comprising the following steps:

positioning a first coupling element on a first limb adjoining the joint, positioning a second coupling element, movable relative to the first coupling element, on a second limb adjoining the joint, and determining the position of the first coupling element relative to the second coupling element using a measuring device.

This method provides according to the invention that the measuring device has at least one reference point rigidly connected to one of the first and second coupling elements, and also has a reference point detection device rigidly connected to the respective other coupling element of the first and second coupling elements, the reference point detection device detecting a plurality of positions of the reference point relative to the reference point detection device during a movement of the first and second limb relative to one another and the at least one characteristic point being determined therefrom.

SUMMARY OF THE INVENTION

According to a development of the method of the invention, the reference point detection device detects a movement path of the respective reference point from the plurality of positions of the reference point.

Furthermore, in a development of the invention, the at least one characteristic point may be determined from the data obtained from the reference point detection device, in particular from the movement path of the respective reference point, as at least one virtual pivotal point for the joint to be measured.

A development of the method according to the invention comprises the step of determining a plurality of characteristic points, preferably as a polar curve, from the data obtained from the reference point detection device, in particular from the movement path of the respective reference point, for the joint to be measured. The method according to the invention further provides that at least two spaced apart reference points, which are rigidly connected to one of the first and second coupling elements, are used, a plurality of positions of the reference points, preferably the movement paths of the at least two reference points relative to the reference point detection device, being detected during a movement of the first and second limb relative to one another.

BRIEF DESCRIPTION OF THE DRAWINGS

The invention will be described hereinafter by way of example with reference to the accompanying figures. In the drawings.

DETAILED DESCRIPTION OF THE PREFERRED EMBODIMENTS

Figure 1:
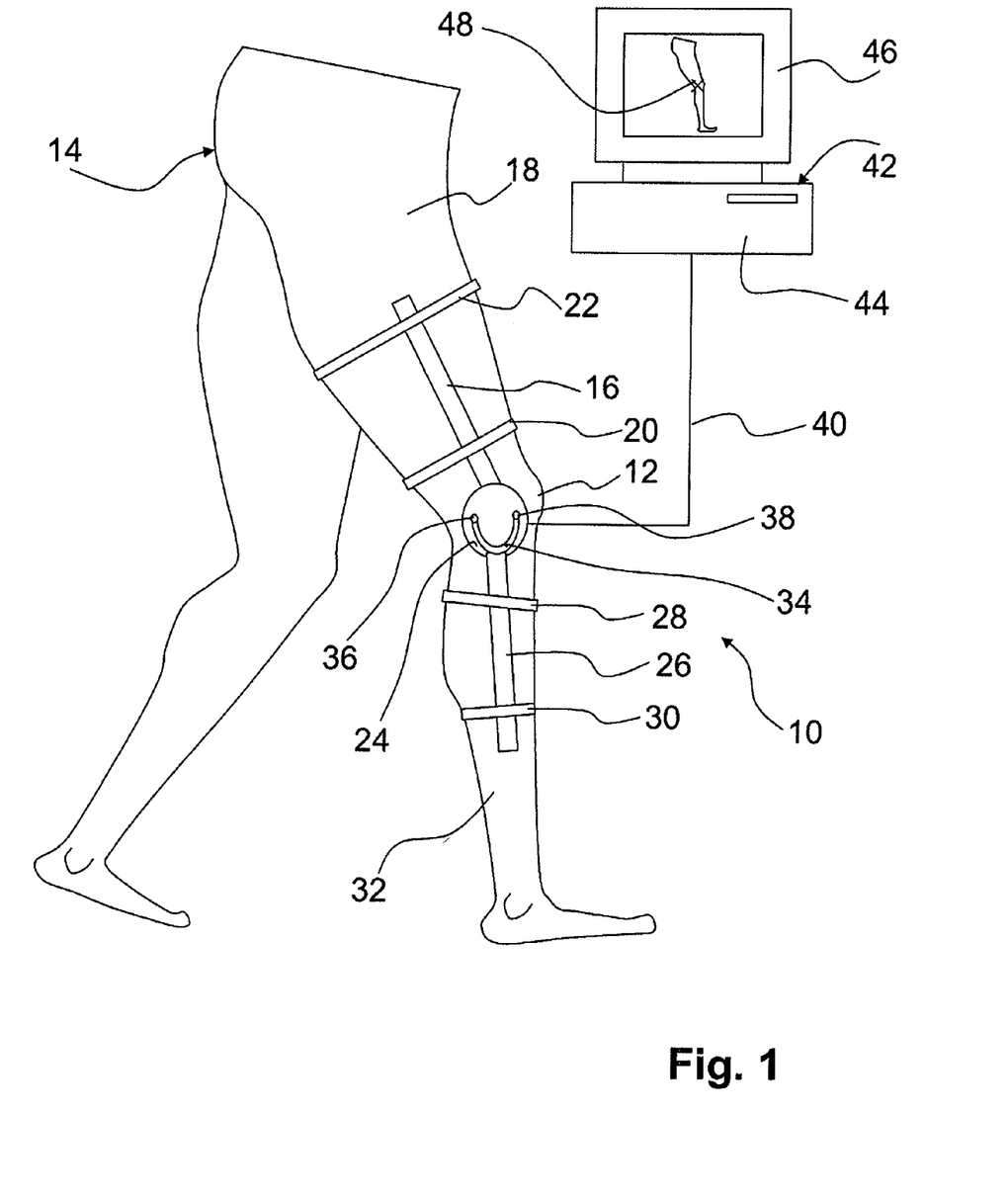
FIG. 1 is an overview for a measuring situation which uses the device according to the invention.

FIG. 1 shows a typical measuring situation in which a device according to the invention generally denoted by reference numeral 10 is used. In the case shown in FIG. 1, the right knee 12 of a patient 14 is gauged in respect of its dynamic behavior by the device according to the invention. Only the lower extremities of the patient 14 are shown.

The device according to the invention comprises a strip-shaped first coupling element 16 which is rigidly connected to the thigh 18 of the right leg of the patient 14. To this end, the first coupling element 16 is tightly secured to the outside of the thigh 18 of the right leg of the patient 14 by two resilient tapes 20, 22. A detection and indication device 24 is firmly positioned on the first coupling element 16. The device 10 according to the invention comprises a second coupling element 26. Said second coupling element, again strip-shaped, is correspondingly rigidly connected to the right lower leg 32 of the patient 14 by two resilient tapes 28, 30. At its end facing the first coupling element 16, the second coupling element 26 has a forked portion 34 rigidly connected to the coupling element 26. Two reference points 36, 38 are provided at the free ends of the forked portion 34. Said reference points 36, 38 are configured such that the position thereof may be detected preferably with an accuracy of a few millimetres by the detection and indication device 24. The detection and indication device 24 is connected to a processing system 42 via a data connection 40. Said processing system 42 comprises a computer unit 44 and an indicator unit 46. The processing system 42 receives the positional data, determined by the detection device 24, of the reference points 36 and 38, stores them and further processes them.

In the measuring situation shown in FIG. 1, the patient 14 makes a step movement. The movements made in the right leg, in particular the movements of the knee joint 12 which lead to a relative movement of the thigh 18 to the lower leg 32 result in a relative movement of the reference points 36, 38 relative to the detection device 24. This relative movement of the reference points 36 and 38, in particular the movement path thereof relative to the detection device 24, is detected by said detection device and transmitted to the processing system 42. Said processing system 42 analyses the movement paths of the reference points 36 and 38 relative to the detection device 24 and determines therefrom at least one characteristic point for the knee joint 12. This characteristic point is, for example, the compromise centre of rotation 48 which is marked by a cross on the indication device 46 and which forms a compromise from the centers of rotation of the knee joint 12 which occur during the movement. A monocentric orthosis, for example, may then be adjusted according to the determined compromise centre of rotation, the orthosis joint thereof being positioned such that its axis of rotation extends through the compromise centre of rotation 48.

The basic principle for the use of the device according to the invention now having been described with reference to FIG. 1, details of various embodiments of the device according to the invention will be described in the following. To avoid repetition and to simplify the description of similar components or components which operate in the same way, the same reference numerals will be used as those in FIG. 1, but suffixed by lower case characters.

Figure 2:
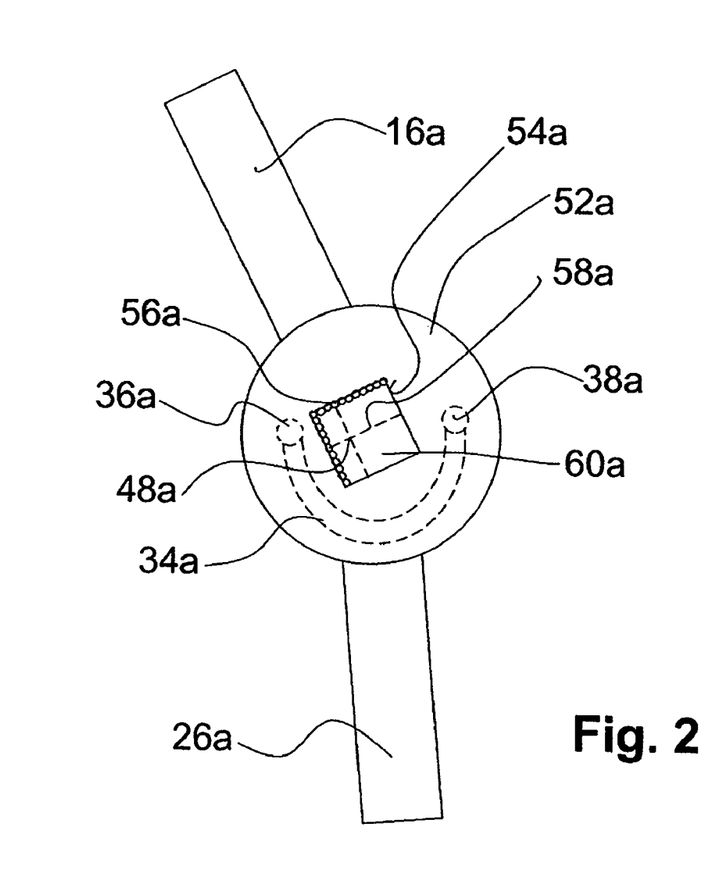
FIG. 2 is a partially cut front view of a first embodiment of the device according to the invention.

FIG. 2 shows a first embodiment of the device according to the invention generally denoted by 10a. In this embodiment, the two coupling elements 16a and 26a are shown shortened although they have substantially the same length as shown schematically in FIG. 1 for positioning or suitably attaching to the thigh and lower leg of a patient. A detection and indication device 52a is rigidly connected to the first coupling element 16a. Said detection and indication device 52a is provided with a rectangular through-opening 54a. A large number of light emitting diodes 56a, arranged in the style of a Cartesian coordinate system, are provided on the inner circumferential surface of the through-opening 54a. The light emitting diodes 56a are configured such that they are able to emit directed beams of light, as shown in FIG. 2 by the beams 58a and 60a shown in dashed lines. The light beams 58a and 60a are directed such that they are able to irradiate the region of the knee joint 12 which may be seen in a top view through the through-opening 54a in the application shown in FIG. 1. The point of intersection of the light beams 58a and 60a may thus be seen on the knee joint 12 of the patient 14. The forked portion 34a is positioned on the second coupling element 26a, as shown schematically in FIG. 2. Said forked portion 34a is accommodated in the detection and indication device 52a so that it may move and pivot in the plane of projection. Attached to the free ends of the forked portion 34a are emitter elements 36a, 38a such that they are in a fixed positional relation with the second coupling element 26a. The emitter elements 36a and 38a form the reference points, the position of which, projected into the plane of projection, may be accurately detected by sensor technology (not shown) inside the detection and indication device 52a.

As generally described hereinbefore with reference to FIG. 1, during a movement of the knee joint 12 and a relative movement resulting therefrom of the two coupling elements 16a and 26a, the relative movement resulting therefrom of the reference points 36a and 38a relative to the detection and indication device 52a is determined. The processing system 42 (not shown in FIG. 2) determines the compromise centre of rotation of the knee joint 12 according to the detected movement paths of the reference points 36a and 38a relative to the detection and indication device 52a, as generally described above with reference to FIG. 1. Additionally or as an alternative to an output at the indication unit 46, the processing system 42, however, activates the diodes 56a such that the two light beams 58a and 60a are generated which meet at point 48a. Point 48a forms the projection of the compromise centre of rotation, determined from the measurements, onto the knee joint 12. The orthopaedic surgeon or orthopaedic technician using the device 10a according to the invention thus receives directly on the knee joint of the patient the compromise centre of rotation specifically determined for this knee joint indicated by the point of intersection 48a, and can there make a colored marking on the patient's skin. This exact patient-dependent determination of the compromise centre of rotation consequently allows an orthosis to be accurately adapted to the patient, so that said orthosis is able to mechanically and functionally stabilize the knee joint 12, to be provided with an orthosis, in an almost optimum manner.

It is obvious that the mode of operation described above, of using the device according to the invention as well as the embodiments and examples of application which will be described in the following, may be employed in the same way for joints other than knee joints of the extremities of a patient.

It should be noted that in a simplified embodiment of the invention, the light emitting diodes 56a may also be used only to indicate coordinates on the coordinate axes of the coordinate cross spanning the rectangular through-opening 54a. An orthopaedic technician is then able to himself determine the point of intersection 48a, for example, by positioning a ruler or a ruler arrangement on the coordinates indicated by the light emitting diodes 56a. In this respect, it is not necessary for the diodes 56a to emit directed light beams intersecting at point 48a.

Figure 3:
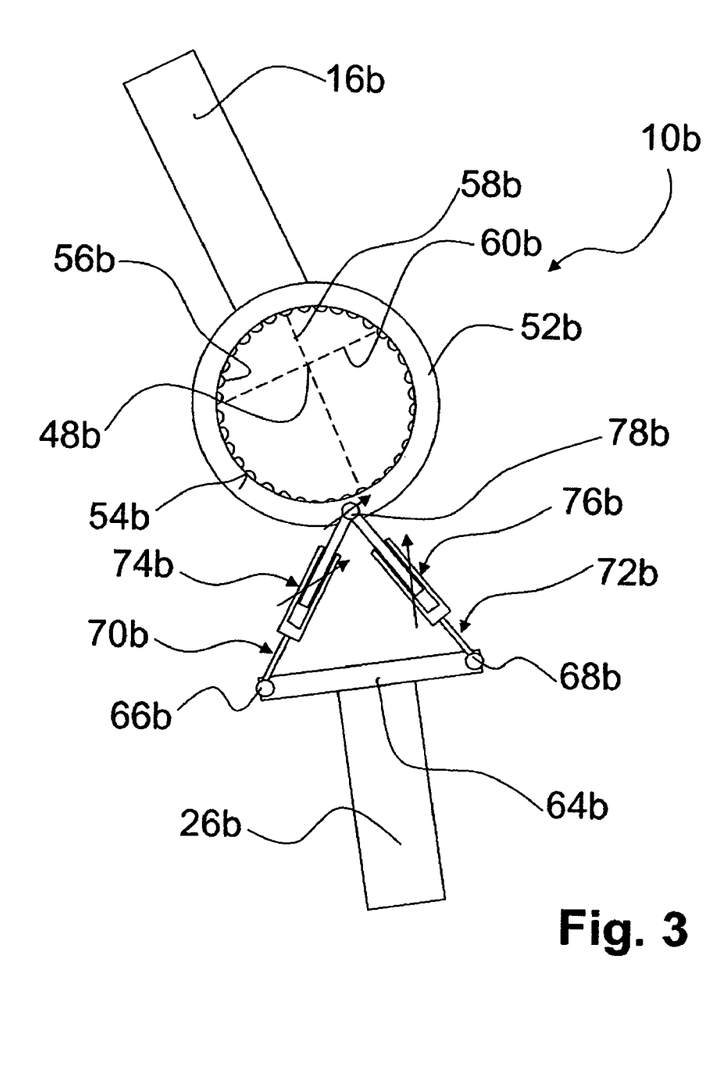
FIG. 3 is a view corresponding to FIG. 2 of a second embodiment, modified with respect to FIG. 2, of the device according to the invention.

FIG. 3 shows a second embodiment of the device according to the invention. Here again, similar components or components which operate in the same way have been given the same reference numerals as for the preceding description but suffixed by lower case "b".

The construction of the first coupling element 16b and of the detection and indication device 52b rigidly connected therewith corresponds substantially to the construction according to FIG. 2 in respect of the arrangement and mode of operation of the diodes 56b. However, the detection and indication device is configured as a detection and indication ring 52b with light emitting diodes positioned in a correspondingly annular manner. Furthermore, the second embodiment according to FIG. 3 differs from the first embodiment according to FIG. 2 in the manner of detecting the relative position of the two coupling elements 16b and 26b with respect to one another. More specifically, in the second embodiment according to FIG. 3, the second coupling element 26b is rigidly connected to a cross strut 64b. Pivotal points 66b, 68b are positioned at the free ends of the cross strut 64b. The cross strut 64b is pivotally connected to connection arms 70b, 72b via the pivotal points 66b and 68b. The connection arms 70b and 72b are telescopic in construction. To this end the two connection arms 70b, 72b have telescopic regions 74b, 76b which make it possible to vary the length of the connection arms 70b and 72b. At their ends remote from the cross strut 64b, the two connection arms 70b, 72b are articulated to the detection and indication ring 52b via another pivotal point 78b.

The pivotal point 78b as well as the two telescopic regions 74b and 76b allow the actual positions to be detected. Thus, as an example, the pivotal point 78b is provided with a rotary potentiometer which detects the instantaneous angular position of the two connection arms 70b and 72b with respect to one another and with respect to the detection and indication ring 52b and transmits these angular positions in a manner not shown to the processing system 42 (see FIG. 1).

The two telescopic regions 74b and 76b are provided with linear potentiometers and thus allows an exact determination of the instantaneous length of the telescopable connection arms 70b and 72b. The linear potentiometers are also connected to the processing system 42 in a manner not shown and output the instantaneous measured values with respect to the length of the connection arms 70b and 72b to said processing system 42.

The relative position of the second coupling element 26b relative to the first coupling element 16b may be determined at any time due to the constant length of the cross strut 64b and the detecting devices at pivotal point 78b (rotary potentiometer) and at the telescopic regions 74b, 76b (linear potentiometer). In the same way as described above with reference to FIGS. 1 and 2, the movement of the ends of the cross strut 64b, i.e. the movement of the pivotal points 66b and 68b to be considered as reference points may thus be detected. A characteristic point for the joint to be measured, in particular the compromise centre of rotation 48b, may in turn be determined from the acquired data and may be indicated on the knee joint to be gauged via the light emitting diodes 56b according to the cross hair principle in the manner described above.

Figure 4:
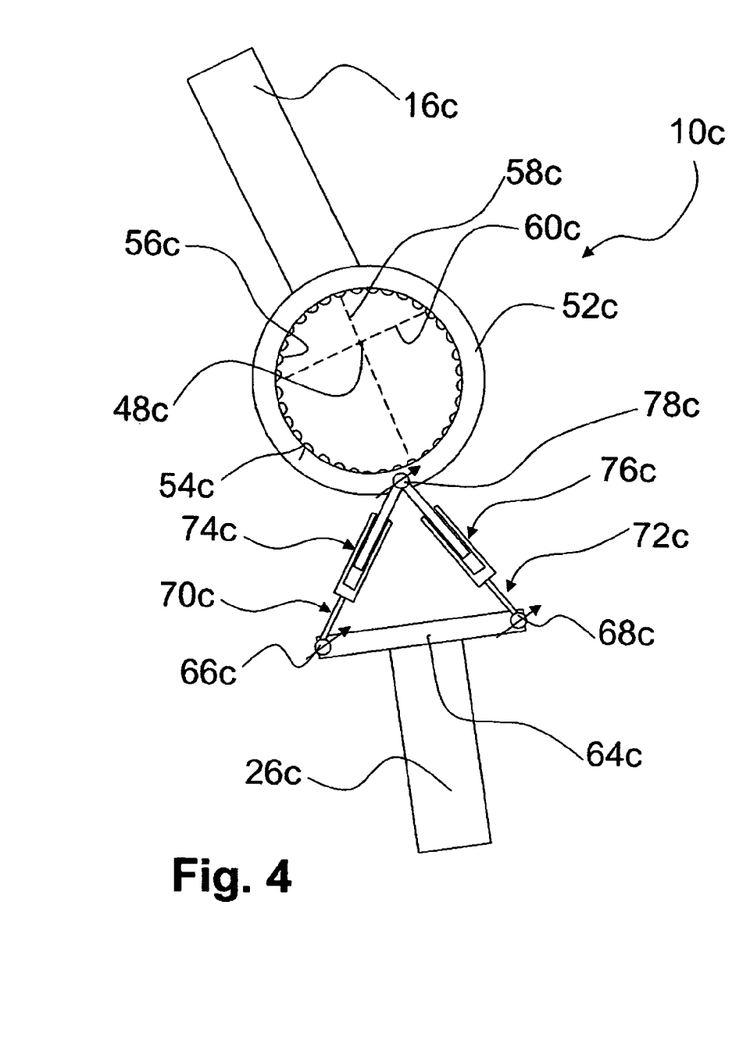
FIG. 4 is a view corresponding to FIG. 3 of a third embodiment, modified with respect to FIG. 3, of the device according to the invention.

FIG. 4 shows a third embodiment of the device according to the invention. Here again, similar or similarly functioning components have been given the same reference numerals, although suffixed with the lower case character "c".

The third embodiment according to FIG. 4 differs from the second embodiment according to FIG. 3 merely in that the two telescopic regions 74c and 76c of the connection arms 70c and 72c are not provided with linear potentiometers. Instead, the two pivotal points 66c and 68c are configured with rotary potentiometers in addition to the pivotal point 78c, so that the angle between the cross strut 64c and the connection arm 70c may be determined via the pivotal point 66c and the angle between the cross strut 68c and the connection arm 72c may be determined by the pivotal points 68c. Accordingly, all three angles at the pivotal points 66c, 68c and 78c may be determined. Moreover, the length of the cross strut 64c is known and remains unchanged. Thus in turn, the position of the coupling element 26c relative to the coupling element 16c may easily be determined and a compromise pivotal point 48c may be calculated from changes in position, which compromise pivotal point 48c may be indicated on the knee joint via the two intersecting light beams 58c and 60c in a manner already described per se.

Figure 5:
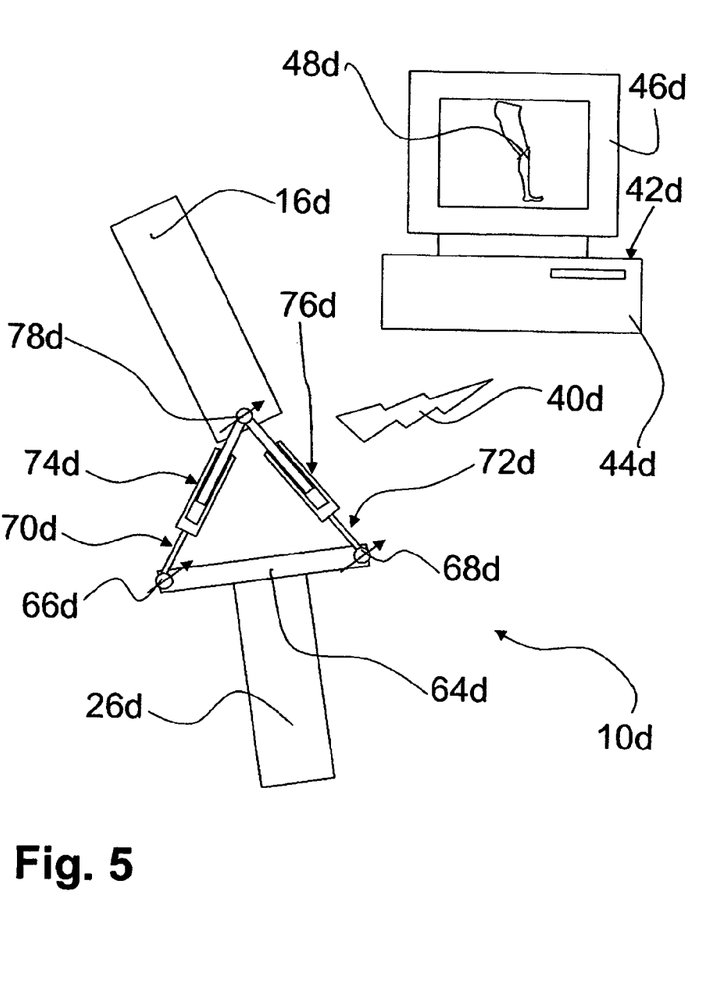
FIG. 5 is a view corresponding to FIGS. 2 to 4 of a simplified fourth embodiment of the device according to the invention.

FIG. 5 shows a fourth embodiment of the arrangement according to the invention. Here again, similar or similarly functioning components have been given the same reference numeral as in the preceding description of the embodiments according to FIGS. 2 to 4, although they are suffixed by lower case character "d".

In the fourth embodiment according to FIG. 5, the detection of the relative position of the two coupling elements 16d and 26d basically operates in the same way as previously described with respect to FIG. 4. The rotary potentiometers positioned in the pivotal points 66d, 68d and 78d allow the determination of the angular positions of the two connection arms 70d and 72d relative to the coupling element 16d, the angular positions between the two connection arms 70d and 72d as well as the angular positions of the two connection arms 70d and 72d relative to the cross strut 64d. The relative position of the two pivotal points 66d and 68d relative to the coupling element 16d may then be determined based on the known length of the cross strut 64d.

In this case, however, the output does not take place directly on the knee joint, as described with reference to FIG. 2 to 4; instead, data is transferred via a, in this case cableless, interface 40d to the processing system 42d. The characteristic point, in particular the compromise centre of rotation 48d, is determined here for the knee joint and is output to the screen 46d. This data may then be used for further documentation or else for the manual or automatic adjustment of an orthosis. Similarly, it is possible for data on a healthy knee joint to be obtained in the manner shown in FIG. 5 and for this data to be evaluated and used to adjust a prosthesis for the patient's other leg to be supplied therewith.

The interface 40d may be configured, for example, as an infrared interface, a Bluetooth interface or as another cableless interface. It is naturally also possible, as already shown schematically in FIG. 1, to couple the device 10d to the processing system 42d via a connection cable.

Figure 6:
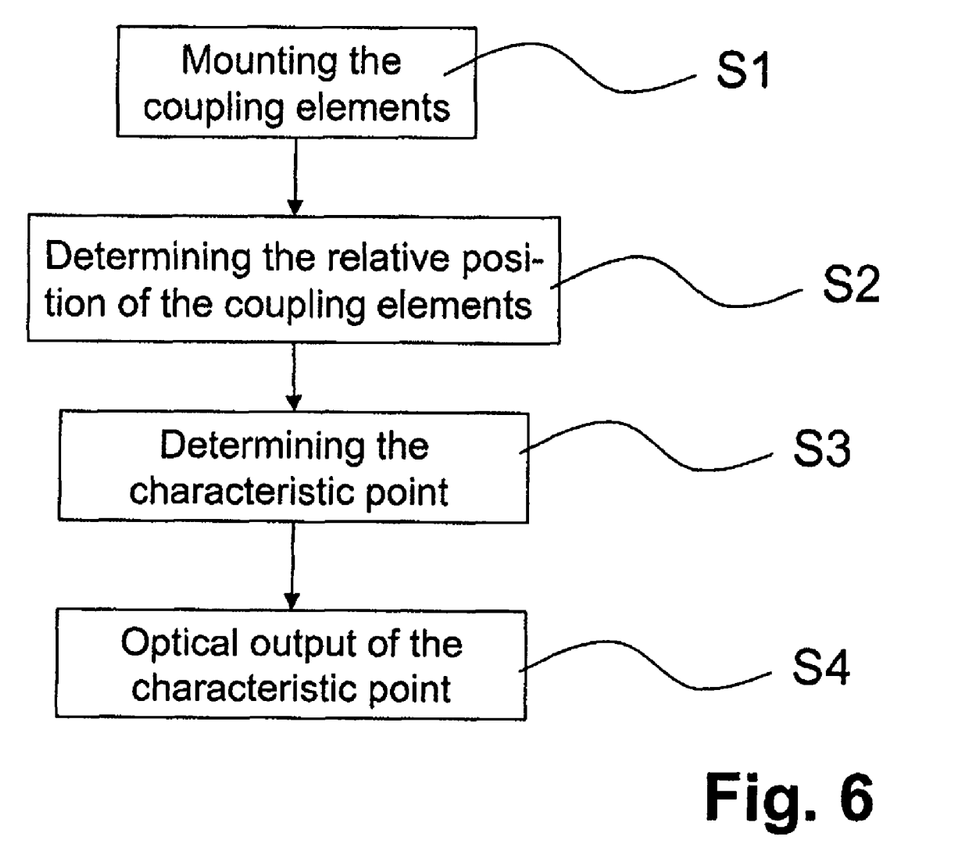
FIG. 6 is a flow chart to illustrate a method according to the invention which uses the device of the invention.

In a schematic flow chart, FIG. 6 shows the mode of operation when the device according to the invention is used. First of all, in step S1, the two coupling elements 16 and 26 are positioned on the limbs of the joint to be measured orthopedically. Then in step S2, the measuring device determines the relative position of the coupling elements 16 and 26 to one another. Thereafter in step S3, a characteristic point, for example a compromise centre of rotation, may then be determined for the respective joint from this relative position of the coupling elements 16 and 26. This compromise centre of rotation is then in step S4 output via a corresponding optical arrangement, for example an LED array according to the previously mentioned cross hair principle or in another manner, for example via a laser or the like, so that the characteristic point may be directly indicated on the joint to be gauged orthopedically.

Figure 7:
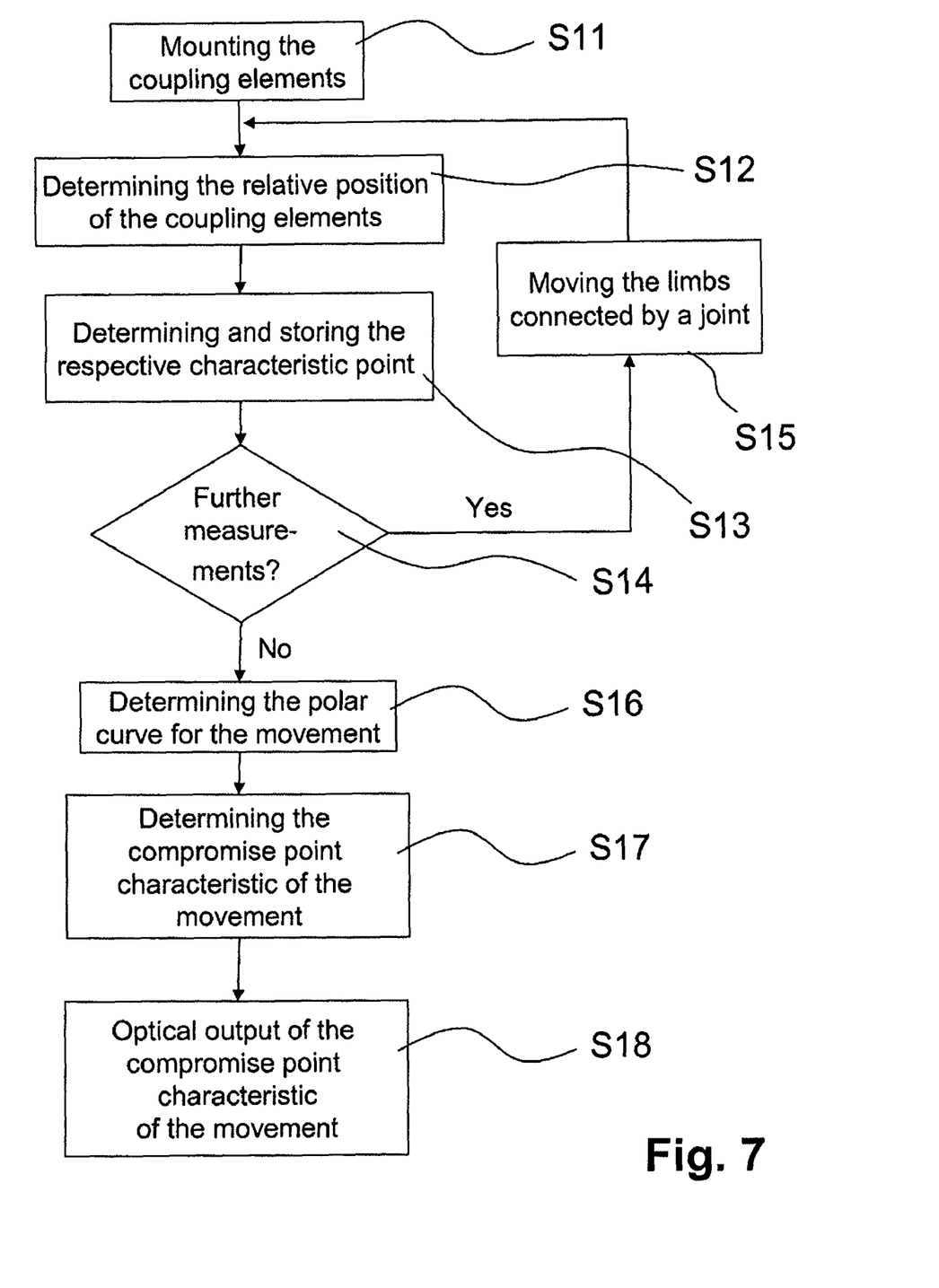
FIG. 7 is a flow chart to illustrate a modification of the method of the invention.

FIG. 7 shows the use of the device 10 according to the invention in a modified form. First of all in step S11, as already described for FIG. 6, the device 10 is positioned on the limbs of the joint to be gauged by securing the two coupling elements 16 and 26 to said limbs. Then here again, in step S12, the relative position of the coupling elements 16 and 26 to one another is determined. This relative position gives the respective characteristic point, for example the compromise centre of rotation, which is stored, as shown in step S13. An enquiry is made in step S14 as to whether further measurements are to be carried out. If this is the case, the joint 12 is moved so that the limbs 18, 32 connected by the joint 12 move with respect to one another and thus the coupling elements 16, 26 also move with respect to one another. The relative position of the coupling elements with respect to one another is again determined in step S12 and, as shown in step S13, the respective characteristic point is determined and stored; further measurements may then be taken, in which case the loop from steps S12, S13, S14 and S15 is run through repeatedly.

When the measuring procedure is at an end, there is no renewed run through the loop. Instead, a polar curve is determined, as shown in step S16, from the determined and stored characteristic points for the movement which has been performed. This polar curve shows the path of the characteristic points, in a specific case of the instantaneous pivotal points, of the two limbs with respect to one another at the various measurement time points.

Then, in step S17, a characteristic compromise point for the detected joint movement, for example a compromise centre of rotation, may be determined from this polar curve. This compromise centre of rotation is selected, for example, such that when an orthosis is used with a monocentric joint for supplying the measured joint with an orthosis, the axis of rotation of the monocentric orthosis joint passes through the determined characteristic compromise point and thus the orthosis stabilizes the measured joint in the best possible way, without also straining it.

When the characteristic compromise point has been determined from the polar curve, said compromise point may in turn be output optically according to step S18, for example according to the cross hair principle, previously described several times, via an LED array or at the processing system 42.

The invention claimed is:

1. Device for determining at least one characteristic point of a joint which joins together two limbs and is to be measured orthopedically, said device compromising: a first coupling element adapted to be attached to a first limb adjoining the joint,
a second coupling element adapted to be pivoted and shifted relative to the first coupling element and adapted to be positioned on a second limb adjoining the joint, and
a measuring device for determining the position of the first coupling element relative to the second coupling element,
wherein the measuring device has at least one reference point which is rigidly connected to one of the first and second coupling elements, and also has a reference point detection device which is rigidly connected to the respective other coupling element of the first and second coupling elements, the reference point detection device having a detector integrated therein for detecting a plurality of positions of the reference point relative to the reference point detection device by an optical, electronic, and/or electromagnetic measurement during a pivoting and shifting movement of the first and second limbs with respect to one another and determining therefrom the at least one characteristic point, and wherein the measuring device includes an indicating device positioned on one of the first and second coupling elements that indicates the at least one determined characteristic point of the joint directly on the joint.

2. Device according to claim 1, wherein the reference point detection device detects a movement path of the respective reference point from the plurality of positions of the reference point.

3. Device according to claim 1, including a processing system which is coupled or adapted to be coupled to the reference point detection device for transmitting data.

4. Device according to claim 3, wherein the processing system is configured to be integral with the device.

5. Device according to claim 3, wherein the processing system determines the at least one characteristic point as at least one virtual pivotal point for the joint to be measured from the data received from the reference point detection device, in particular from the movement path of the respective reference point.

6. Device according to claim 3, wherein the processing system determines a plurality of characteristic points, from the data received from the reference point detection device, in particular from the movement path of the respective reference point.

7. Device according to claim 1, including at least two mutually spaced apart reference points which are rigidly connected to one of the first and second coupling elements, the reference point detection device detecting a plurality of positions of the at least two reference points relative to the reference point detection device during a movement of the first and second limbs with respect to one another.

8. Device according to claim 1, wherein the indicating device comprises an optical output means which is able to optically indicate the at least one determined characteristic point of the joint on the joint to be measured.

9. Device according to claim 8, wherein the output means comprises an angled arrangement of a plurality of light sources, by which directed light beams may be emitted, it being possible to indicate the at least one determined virtual pivotal point by a point of intersection of the two light beams.

10. Device according to claim 8, wherein the output means has an arrangement of a plurality of light sources, which indicate contact points, in particular for positioning a gauging arrangement, in particular a ruler arrangement, it being possible to mark out on the joint the at least one determined virtual pivotal point by eye or by suitably positioning the gauging arrangement.

11. Device according to claim 1, wherein the indicating device comprises an electromechanical output means having an electromechanically displaceable mark adapted to indicate the at least one determined characteristic point on the joint by suitably positioning the electromechanically displaceable mark.

12. Device according to claim 11, including a marking device, in particular a pencil, that can make a colored mark on the joint at the at least one determined characteristic point following suitable electromechanical displacement of the electromechanically displaceable mark.

* * * * *